United States Patent
Nicolas et al.

(10) Patent No.: US 7,139,417 B2
(45) Date of Patent: Nov. 21, 2006

(54) COMBINATION COMPRESSION AND REGISTRATION TECHNIQUES TO IMPLEMENT TEMPORAL SUBTRACTION AS AN APPLICATION SERVICE PROVIDER TO DETECT CHANGES OVER TIME TO MEDICAL IMAGING

(75) Inventors: Francois S. Nicolas, Impasse du moulin de Jubiciaux (FR); Vianney P. Battle, Milwaukee, WI (US); Kenneth S. Kump, Waukesha, WI (US); Christopher D. Unger, Delafield, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 812 days.

(21) Appl. No.: 09/682,290

(22) Filed: Aug. 14, 2001

(65) Prior Publication Data

US 2003/0035584 A1 Feb. 20, 2003

(51) Int. Cl.
*G06K 9/00* (2006.01)
*G06K 9/36* (2006.01)
*G06F 15/16* (2006.01)

(52) U.S. Cl. .................. 382/131; 382/232; 709/247

(58) Field of Classification Search ........ 382/232–233, 382/130–133, 235, 244, 128, 239; 345/555; 348/384.1; 358/426.01, 487; 375/240; 708/203; 600/407; 705/3, 203; 709/203, 247

See application file for complete search history.

(56) References Cited

U.S. PATENT DOCUMENTS

| | | | | |
|---|---|---|---|---|
| 5,384,643 | A * | 1/1995 | Inga et al. | 358/403 |
| 5,416,602 | A * | 5/1995 | Inga et al. | 358/403 |
| 5,825,830 | A * | 10/1998 | Kopf | 375/340 |
| 5,987,345 | A * | 11/1999 | Engelmann et al. | 600/407 |
| 5,991,816 | A * | 11/1999 | Percival et al. | 709/247 |
| 6,091,777 | A * | 7/2000 | Guetz et al. | 375/240.11 |
| 6,206,021 | B1 * | 3/2001 | Hartman et al. | 137/15.06 |
| 6,353,487 | B1 * | 3/2002 | Fredlund et al. | 358/487 |
| 6,755,787 | B1 * | 6/2004 | Hossack et al. | 600/447 |
| 6,757,413 | B1 * | 6/2004 | LeMahieu | 382/128 |
| 6,832,199 | B1 * | 12/2004 | Kucek et al. | 705/2 |
| 6,901,371 | B1 * | 5/2005 | Koritzinsky et al. | 705/2 |
| 6,909,792 | B1 * | 6/2005 | Carrott et al. | 382/128 |
| 2002/0019751 | A1 * | 2/2002 | Rothschild et al. | 705/3 |
| 2003/0059096 | A1 * | 3/2003 | Dekel et al. | 382/131 |

* cited by examiner

*Primary Examiner*—Duy M. Dang
(74) *Attorney, Agent, or Firm*—Fletcher Yoder

(57) ABSTRACT

The present technique involves remote processing and comparison of medical diagnostic images obtained over a period of time. A remote processing system is provided to match and subtract the medical diagnostic images, which may be received from users and gathered from remote image storage systems. Users are able to interact with the remote processing system through uniform interfaces, which may be disposed at medical institutions to provide platform independent interaction with, and remote processing by, the remote processing system. The technique also uses compression routines to facilitate network transfers of images between the uniform interface and the remote processing system.

85 Claims, 7 Drawing Sheets

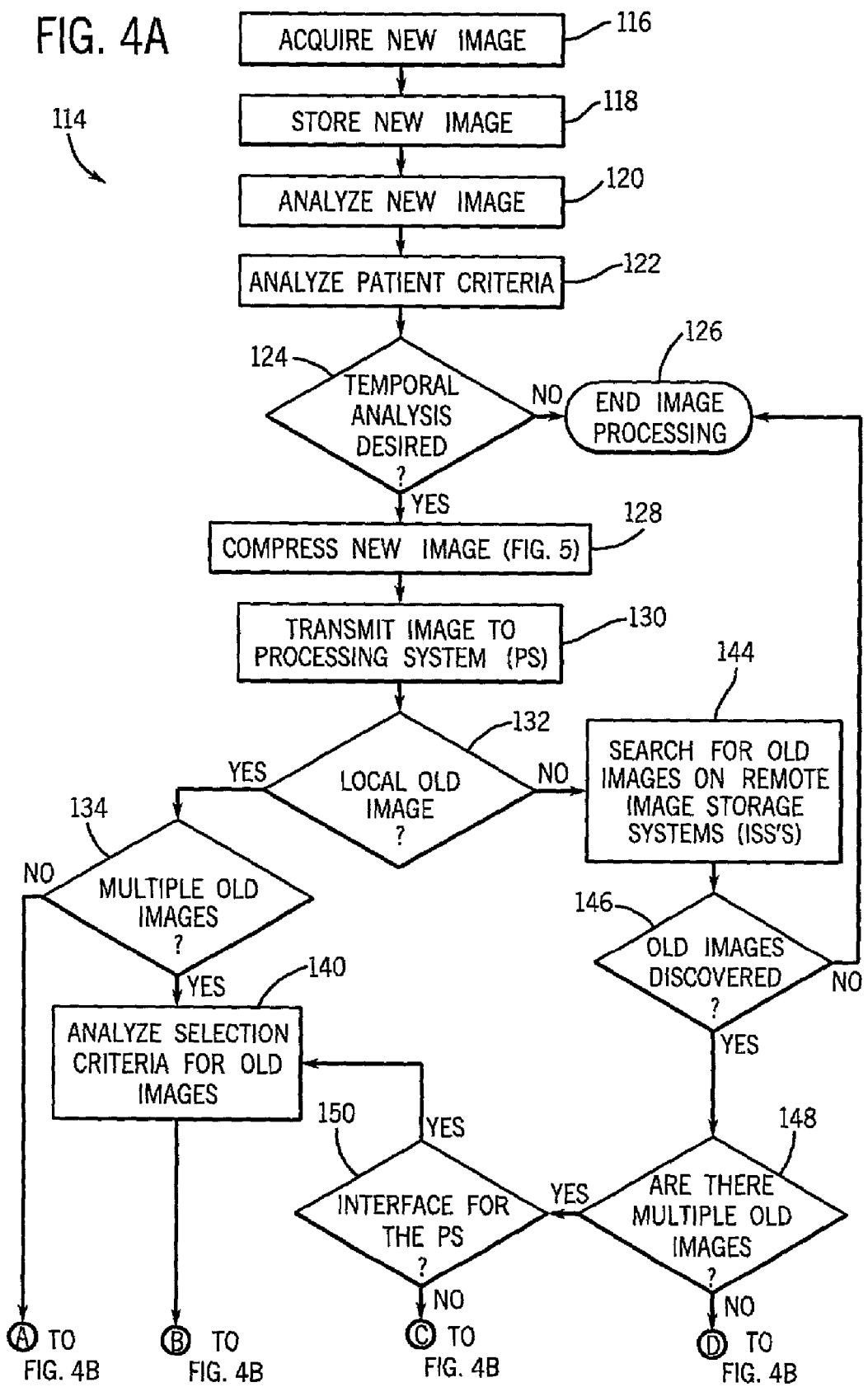

COMBINATION COMPRESSION AND REGISTRATION TECHNIQUES TO IMPLEMENT TEMPORAL SUBTRACTION AS AN APPLICATION SERVICE PROVIDER TO DETECT CHANGES OVER TIME TO MEDICAL IMAGING

BACKGROUND OF THE INVENTION

The present invention relates generally to medical diagnostic imaging systems and, more particularly, to a technique for temporal analysis of images. The present technique utilizes image compression techniques and a remote applications server to perform image matching and subtraction remotely and independently from the client-side computing system.

Medical diagnostic and imaging systems are ubiquitous in modern health care facilities. Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. Such systems provide invaluable tools for identifying, diagnosing and treating physical conditions and greatly reduce the need for surgical diagnostic intervention. In many instances, these modalities complement one another and offer the physician a range of techniques for imaging particular types of tissue, organs, physiological systems, and so forth. Health care institutions often dispose of several such imaging systems at a single or multiple facilities, permitting its physicians to draw upon such resources as required by particular patient needs. In many instances, final diagnosis and treatment proceeds only after an attending physician or radiologist has complemented conventional examinations with detailed images of relevant areas and tissues via one or more imaging modalities.

It is often desirable to compare physiological images of a patient over a period of medical treatment to evaluate any physiological changes in the patient, the progress of a disease (e.g., cancer), or the effectiveness of a medical treatment. The present approach is to use image subtraction techniques to obtain an image highlighting the temporally changed areas in a series of medical images. For example, an image obtained six months ago may be subtracted from a current image to highlight (or reveal) a cancerous growth in a subject. Unfortunately, the images may be stored at many different health facilities in which the patient sought treatment and/or medical imaging. Moreover, each facility may have different operating systems, medical systems, image storage systems and so forth. These incompatibilities and the geographically scattered storage of medical images complicate the temporal analysis of medical diagnostic images, which are typically stored as very large files (e.g. 10 MB).

Accordingly, there is a need for a technique for temporal analysis of medical diagnostic images that is independent of the particular platform utilized at a medical facility. More particularly, a technique is needed for remotely processing medical diagnostic images and for integrating medical imaging and storage systems at a plurality of medical facilities.

SUMMARY OF THE INVENTION

The present technique involves remote processing and comparison of medical diagnostic images obtained over a period of time. A remote processing system is provided to match and subtract the medical diagnostic images, which may be received from users and gathered from remote image storage systems. Users are able to interact with the remote processing system through uniform interfaces, which may be disposed at medical institutions to provide platform independent interaction with, and remote processing by, the remote processing system. The technique also uses compression routines to facilitate network transfers of images between the uniform interface and the remote processing system. An aspect of the present technique provides a method for processing images produced by medical diagnostic imaging systems. The method includes compressing at least one image of a plurality of temporally distinct medical images of desired physiological features. The method also includes transmitting the plurality of temporally distinct medical images to a remote processing system via a network. An image is also generated from the plurality of temporally distinct medical images to highlight temporal differences of the desired physiological features between the image pair.

Another aspect of the present technique provides a method for temporal analysis of medical diagnostic images. The method includes compressing a plurality of temporally distinct medical diagnostic images of desired physiological features. The plurality of temporally distinct medical diagnostic images are then electronically transmitted to a remote processing system. At the remote processing system, the desired physiological features of at least two images of the plurality of temporally distinct medical diagnostic images are geometrically matched. The method also includes generating an image from the at least two images to highlight physiological differences between the at least two images.

Another aspect of the present technique provides a method for remotely performing a comparative analysis of a plurality of medical diagnostic images obtained over a time period. The method includes gathering medical diagnostic images at a remote processing system via a network. At least two images of the medical diagnostic images are then processed at the remote processing system to generate a temporal analysis image illustrating physiological differences between the at least two images.

Another aspect of the present technique provides a system for remotely processing medical diagnostic images. The system includes a remote processing system configured to compare a plurality of medical images and to highlight temporal differences between at least two images of the plurality of medical images. The system also has a uniform interface for interacting with the remote processing system via a network. An image compression module, which is accessible by the uniform interface, is also provided for compressing at least one image of the plurality of medical images.

Another aspect of the present technique provides a system for platform independent processing of medical diagnostic images. The system includes an applications server configured to execute temporal image analysis requests from remote platform independent interfaces. The applications server has an image matching module configured for geometrically matching desired physiological features in at least two images obtained over a time period. The applications server also has an image subtraction module configured for subtracting a first image from a second image of the at least two images.

BRIEF DESCRIPTION OF DRAWINGS

The foregoing and other advantages of the invention will become apparent upon reading the following detailed description with reference to the drawings in which:

FIGS. 4A & 4B are flow charts illustrating an exemplary image processing routine of the present technique;

DETAILED DESCRIPTION

Figure 1:
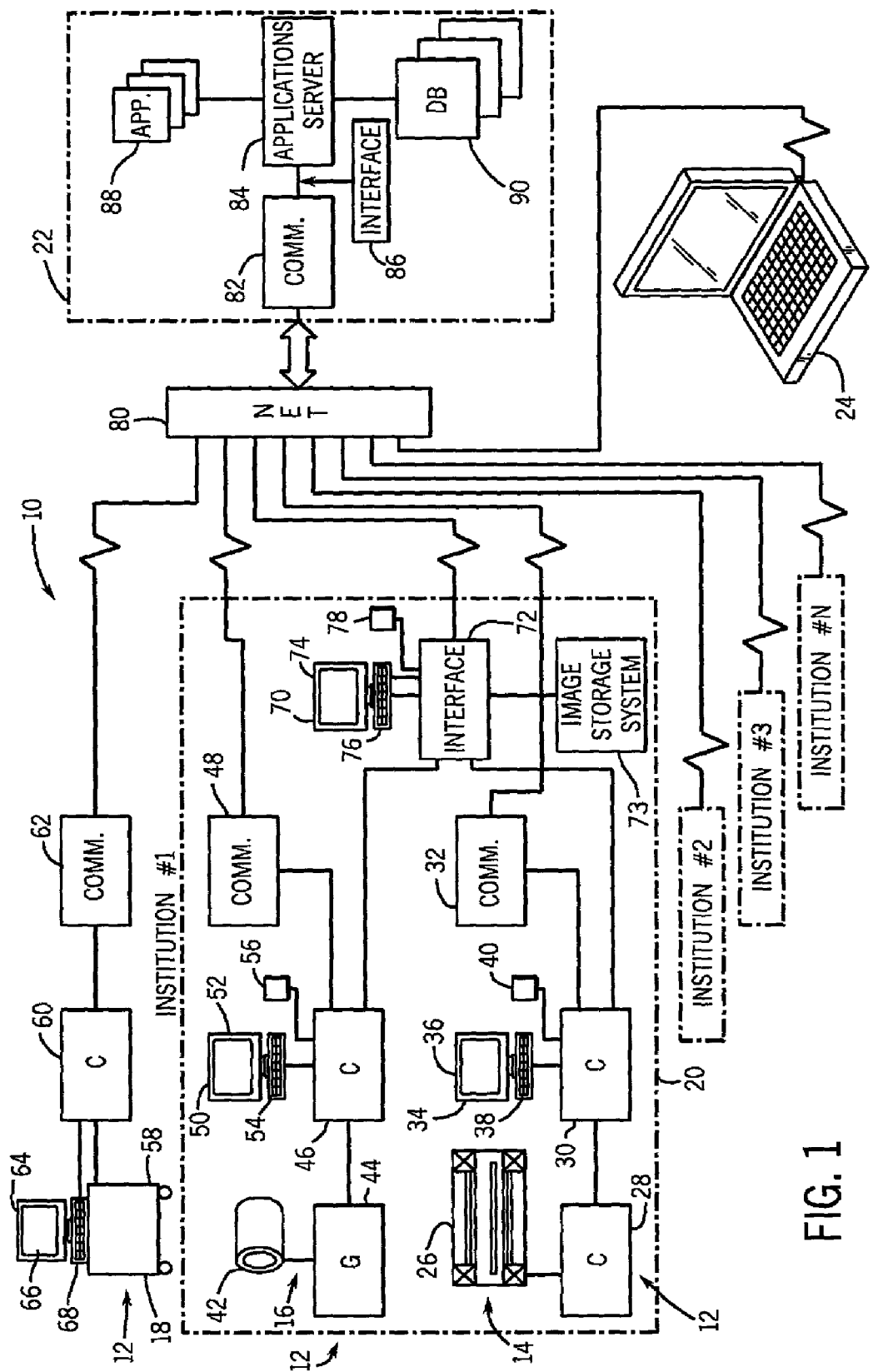
FIG. 1 is a diagram of the present technique, illustrating an exemplary system for communication and data exchange between a plurality of medical clients and a data processing center remote from the medical clients.

Turning now to the drawings, and referring first to FIG. 1, a communication system 10 is illustrated for providing remote data processing for a plurality of healthcare providers having a plurality of medical resources, such as medical diagnostic systems 12. In the embodiment illustrated in FIG. 1, the medical diagnostic systems 12 include a magnetic resonance imaging (MRI) system 14, a computed tomography (CT) system 16, and an ultrasound imaging system 18. The diagnostic systems 12 may be positioned in a single location or facility, such as institutions #1 through #N (e.g., medical facility 20), or may be remote from one another as illustrated for ultrasound imaging system 18. Each medical facility also may gain remote access to a data processing center 22 via the communication system 10. The data processing center 22 also may be accessible via a remote client unit 24. Accordingly, the present technique provides a uniform interface (e.g., thin client or other platform independent interface) for interacting with the data processing center 22 to serve multiple clients, facilities and imaging systems.

In the exemplary embodiment of FIG. 1, several different medical clients (e.g., institutions #1 through #N) are provided with remote access to the data processing center 22. These and other medical clients may be provided access to, and benefit from, the data processing center 22, depending upon the capabilities of the data processing center 22, and other factors. However, the present technique is particularly well suited for remotely processing client data (e.g., images) associated with a wide variety of medical diagnostic system modalities, including MRI systems, CT systems, ultrasound systems, positron emission tomography (PET) systems, nuclear medicine systems, and so forth. Moreover, the medical clients utilizing the data processing center 22 in accordance with the present techniques may be in different medical fields, may have different medical resources, and may have different types of patients. For example, medical resources may include a variety of medical equipment, systems, instruments and human resources for a particular medical procedure or medical practice. Furthermore, medical resources may include real estate, office space, healthcare service capacity, and financial resources of a particular institution. A variety of client data may be transmitted to the data processing center 22 via the communication system 10. For example, the client may transmit images generated by medical diagnostic imaging systems, patient files from a computer, or data entered from a client computer (e.g., a thin client) coupled to the communication system 10 (e.g., remote client unit 24).

The medical resources, as noted above, may comprise a variety of medical systems. Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. The system controller 30 also may include a uniform platform for interactively exchanging client data and processing requests with data processing center 22. The system controller 30 is linked to a communications module 32, which may be included in a single or separate physical package from system controller 30. System controller 30 is also linked to an operator station 34, which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally. Accordingly, it should not be limited to image data acquisition, to picture archiving communications and retrieval systems, nor to image management systems, facility or institution management systems, or viewing systems and the like, in the field of medical diagnostics. More particularly, the medical resources may include imaging systems, clinical diagnostic systems, physiological monitoring systems, and so forth.

Similarly, CT system 16 will typically include a scanner 42, which detects portions of x-ray radiation directed through a subject of interest. Scanner 42 is coupled to a generator and controller, as well as to a signal acquisition unit, represented collectively as reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for processing at the data processing center 22. Also, the system controller 46 is coupled to an operator station 50, which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest and for acquiring resultant signals, which are processed to reconstruct a useful image. The system includes a system controller 60, which regulates operation of scanner 58 and which processes acquired signals to reconstruct the image. Moreover, system 18 includes a communications module 62 for transmitting client data and processing requests between system controller 60 and the data processing center 22. System 18 also includes an operator's station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated embodiment. The management system may be coupled to the system controllers in an Intranet configuration, in a file sharing configuration, a client/server arrangement, or in any other suitable manner. The management system also has an interface 72, such as a thin client or other suitable computing hardware and software, for communicating and interacting with the data processing center 22. An image storage system 73 is also networked to the interface 72 to provide image storage and retrieval of medical diagnostic images obtained by the various imaging systems. Moreover, management station 70 will typically include a monitor 74 for viewing system operational parameters, analyzing system utilization, and exchanging client data and processing information between the facility 20 and the data processing center 22. Input devices, such as a standard computer keyboard 76 and mouse 78, may also be provided to facilitate user interaction. It should be noted that, alternatively, the management system, or other diagnostic system components, may be "stand-alone," i.e., not coupled directly to a diagnostic system. Although the data processing center 22 may require a variety of client data (e.g., patient images, medical history, processing criteria, etc.) to fully process a client request, the client data may include medical data that is not derived directly from the medical system (e.g., CT and MRI systems). The client data may simply be transmitted from a client computer (e.g., remote client unit 24) after having been entered by the medical client. For example, the client data may be entered via an electronic form, or web interface.

The communication modules mentioned above, as well as workstation 72 and remote client unit 24, may be linked to data processing center 22 via a remote access network 80. For this purpose, any suitable network connection may be employed. Presently preferred network configurations include proprietary or dedicated networks, as well as open networks, such as the Internet. Data may be exchanged between the institutions, medical resources, client computers and the remote data processing center 22 in any suitable format, such as in accordance with the Internet Protocol (IP), the Transmission Control Protocol (TCP), or other known protocols. Moreover, certain portions of the data may be transmitted or formatted via markup languages such as the HyperText Markup Language (HTML), Extensible Markup Language (XML), or other Internet and communication languages. Exemplary interface structures and communications components are described in detail below.

At the data processing center 22, messages, client requests and client data are received by communication components 82 and are transmitted to processing system 84 (e.g., an applications server or an applications service provider) via an interface 86. For example, in the present technique, the data processing center 22 may receive, handle and process old and new images, patient data and other processing criteria to process the desired medical images. In general, the processing system 84 may include one or a plurality of computers, as well as dedicated hardware or software servers for processing the various requests and for receiving and transmitting the information, as described more fully below. The data processing center 22 also may include a plurality of applications 88 and databases 90. The applications 88 may include image compression and decompression applications, encryption and other security applications, image matching and registration applications, image subtraction applications and various other applications for analyzing and processing patient records, exams, images and medical data. The databases 90 also may include extensive database information on medical resources (e.g., medical diagnostic imaging systems), a particular medical facility, patient medical records, and so forth. As described below, the applications 88 and databases 90 may be employed both for analyzing the client data (e.g., images) and for processing the request (e.g., image matching and subtraction) transmitted to the processing system 84 by the client. The processing system 84 and a portion of the applications 88 also may be disposed on a web server. For example, the processing system 84 may include an Internet based image processing program configured to guide a client through the steps of compression, matching and subtraction.

Figure 2:
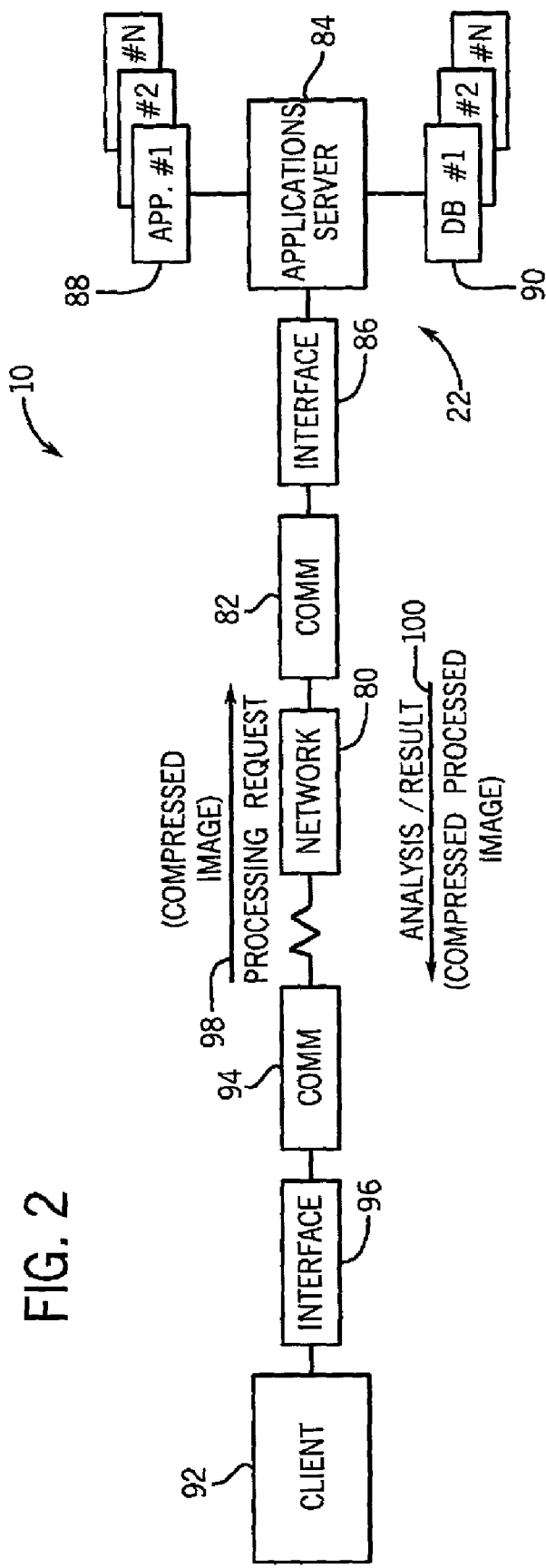
FIG. 2 is a diagram of the present technique, illustrating an exemplary data flow between the data processing center and a client.

FIG. 2 is a diagram of the communication system 10, illustrating an exemplary data flow between a client 92 and the data processing center 22. The client 92 may be a medical facility, institution or other individual requiring image processing of medical images. The data processing center 22 may be associated with a medical supplier, a medical institution, or some other entity located remote from the client 92. The client 92 can communicate with the data processing center 22 via a communication device 94, which connects to the network 80 and the communication components 82 for the data processing center 22. The communication device 94 may be a modem, a DSL or Ethernet device, or any other suitable network device. The client 92 then can interact with the processing system 84 by using any suitable interface 96, such as a thin client or other platform independent interface.

In this exemplary embodiment, the client 92 interacts with the data processing center 22 via the interface 94. The interface 94 may be used to determine if image processing is necessary and also to provide the appropriate images and data to the data processing center 22 for image processing. Accordingly, the client 92 enters data, makes appropriate selections, and transmits a processing request 98 along with the appropriate new images and old images (if local) to the data processing center 22. In the present technique, the images are compressed before being electronically transferred to the data processing center 22. By compressing the images, the size of the images may be reduced sufficiently (e.g., from 15, 10, 5 or 2 MB down to 1.5 or 1 MB) to decrease the transfer time for the processing request 98. The images and corresponding request 98 also may be encrypted prior to electronic transfer. Accordingly, the processing request 98 is routed through the network 80 to the data processing center 22, which may include a plurality of computer systems, servers, workstations, databases, and other hardware and software applications necessary for processing the images and the corresponding data and processing criteria. As illustrated, the interface 86 is provided to facilitate interaction with the processing system 84. The interface 86 may include various hardware and software, such as a web interface (e.g., Internet pages and forms), to facilitate proper data handling and processing by the processing system 84 utilizing the applications 88 and databases 90.

In this exemplary embodiment, the server or processing system 84 has appropriate applications 88 (e.g., applications #1 through #N) and databases 90 (e.g., databases #1 through #N) for analyzing the processing request 98. Accordingly, an image compression/decompression program, an image matching/registration program, and an image subtraction program may be disposed on the processing system with one or more medical resource databases. Using these applications 88 and databases 90, the processing system 84 generates a processed image 100 that highlights temporally changed features between old and new medical images. In the present technique, at least one of the old and new images is transmitted to, or retrieved by, the processing system 84 in a compressed format (e.g., using various compression techniques). If the client 92 has the interface 96, then the new image(s) may be compressed on the client-side prior to electronic transfer over the network 80. However, the old image may not be local to the client 92 or it may not be disposed at a medical facility having the interface 96. In this situation, the image may be compressed on the server-side prior to image matching, subtraction, and other image processing by the processing system 84. Alternatively, both the old and new images may be compressed/decompressed to a desired size/resolution on the server-side prior to image processing. If the processed image 100 is not in a compressed format, then the processing system 84 may perform image compression before transmitting the processed image 100 back to client 92. The present technique also may utilize a variety of security applications and hardware to protect the images, requests and results being communicated over the communication system 10.

The processed image 100 (e.g., a compressed processed image) and the corresponding analysis and results are then transmitted to the client 92 via the communication system 10. The analysis and results may be formatted by the processing system 84, or they may be transmitted as unformatted data for subsequent formatting by a client server or web server. For example, the data processing center 22 may generate user viewable pages (e.g., Internet pages) based on the analysis. The client may then view the pages via the interface 96, which may include an Internet browser and other image software. It should also be noted that the data processing center 22 may provide the analysis and results as a customer-tailored report, which may incorporate a variety of customer information, system parameters and other unique characteristics of the particular customer.

Figure 3:
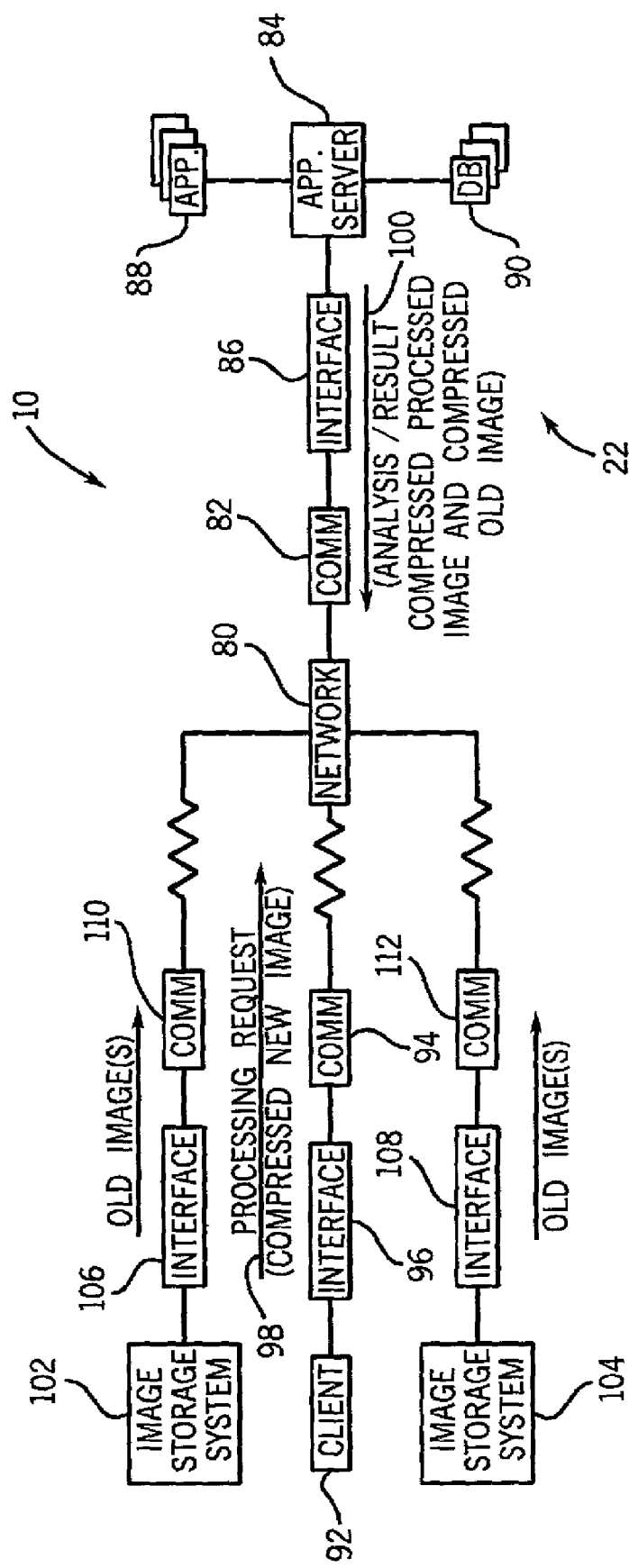
FIG. 3 is a diagram of the present technique, illustrating an alternate data flow between the data processing center, the client and image storage systems.

Although each client 92 may independently communicate with the data processing center 22 to remotely process medical diagnostic images, the present technique also may involve interaction between a plurality of clients and the data processing center 22, as illustrated in FIG. 3. The plurality of clients may comprise multiple modalities (e.g., CT, MRI, Ultrasound, etc.), multiple business entities, multiple operating systems, and various other differences. FIG. 3 illustrates an alternate data flow and image processing scheme, which integrates the client 92, the data processing center 22, and image storage systems 102 and 104. As illustrated, the client 92 communicates through the network 80 via the communication component 94 and interacts with the data processing center 22 via the interface 96. The image storage systems 102 and 104 communicate through the network 80 via communication components 110 and 112 and interact with the data processing center 22 via interfaces 106 and 108, respectively. The data processing center 22 also has the interface 86, as discussed above, to facilitate remote user interaction with the processing system 84 and the corresponding applications 88 and databases 90.

Accordingly, the client 92 may obtain a new image from a medical diagnostic imaging system, and then compress the new image to facilitate electronic transfer over the network 80 and to the processing system 84. Once the client 92 has obtained a new medical diagnostic image, it may be desirable to analyze any changes in the image over a time period. For example, if the subject has obtained prior medical diagnostic imaging procedures, then it may be desirable to compare the prior and new medical diagnostic images to determine if there are any physiological changes in the subject (e.g., a cancerous growth in an organ). The client 92 may determine if such temporal analysis is necessary or desired, or the client 92 may simply send the new image and corresponding patient information to the data processing center 22 for analysis. Accordingly, the client 92 may transmit the processing request 98, including the compressed new image, to the data processing center 22 via the interface 96.

As discussed above, the interface 96 may be a thin client or other platform independent interface for remote communication with the data processing center 22, which has the actual applications for processing the image. The typical medical diagnostic image has a relatively large file size, such as 10 MB. Therefore, the present technique utilizes compression techniques to reduce the file size and to increase the transfer speed over the network 80. If the client 92 also has an old image of the subject stored on the image storage system 73, then the client 92 may compress and transmit the old medical diagnostic image to the processing system 84 via the interface 96. However, as illustrated in FIG. 3, the client 92 may not have an old medical diagnostic image stored locally in the image storage system 73.

When the processing request 98 is received at the data processing center 22, the processing system 84 performs a search for old medical diagnostic images over the network 80 to locate images stored at other medical facilities, such as medical facilities having the interfaces 106 and 108 and image storage systems 102 and 104, respectively. If the processing system 84 locates one or more old images on the image storage systems 102 and 104, then the old images may be automatically retrieved from the image storage systems 102 and 104 and transmitted to the processing system 84. The images, which may correspond to one or more medical modalities, may then be used for image matching and subtraction between the old and new medical diagnostic images. It should also be noted that the old images located on the image storage systems 102 and 104 may be compressed prior to electronic transfer to the processing system 84.

If the image storage systems 102 and 104 are not coupled to interfaces 106 and 108, such as where the image storage systems 102 and 104 are located in medical facilities having incompatible hardware or software and no interface, then the old images may simply be retrieved in the full uncompressed format by the processing system 84. However, the processing system 84 may then compress the old images to the same compression format as the new images received by the processing system 84. Image matching and subtraction can then be performed on the old and new images in the compressed format.

The processing system 84 also may automatically determine the best, or most suitable, of the old images to use in the image processing routine. For example, the processing system 84 may analyze prior health care and various other factors to determine which old image would provide the best results for the image subtraction routine.

The processing system 84 then performs image matching and subtraction to provide a processed image highlighting the changed physiological features in the subject over time. Once the processing system 84 has processed the image(s), the processing system 84 transmits the results 100 to the client 92 via the network 80. The client 92 may then view the processed image on the interface 96, which may include a variety of imaging software such as an Internet browser. The processed image may be transmitted over the network 80 in a full resolution (uncompressed) format or in a compressed format. The compressed format may be the same format as those of the old and new images processed by the processing system 84. It should also be noted that the processing system 84 may perform any number of the image processing steps, while the remainder of the processing steps may be performed on the client-side with the local computing components of the client 92. The processing system 84 also may transmit one or more of the old images retrieved from the image storage systems 102 and 104 and it may transmit a deformation field for the image matching process and various other processing data. Accordingly, the present technique facilitates integration between the client 92 and the data processing center 22 and a plurality of other remote medical facilities and image storage systems.

Figure 4B:
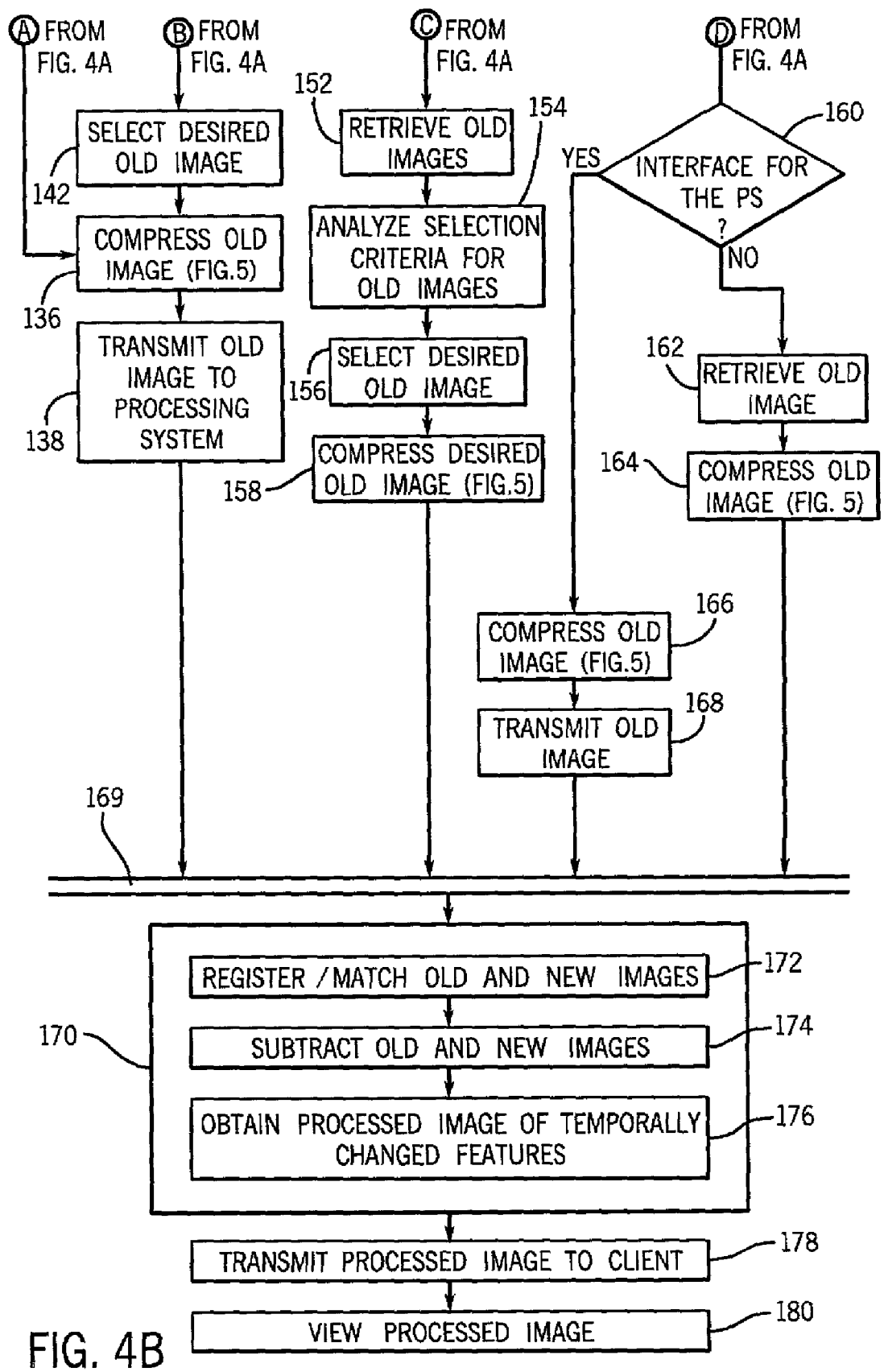

The present technique utilizes image compression, the client interface, and the remote processing scheme to provide platform independent image processing for integrating remote medical imaging and storage systems. Accordingly, the present technique performs various processing functions on the remote server-side, while reserving some platform independent tasks for the client-side. As illustrated in the image processing scheme 14 of FIGS. 4A and 4B, the client 92 may acquire a new medical diagnostic image (block 116) from one of the medical diagnostic imaging systems and then store the new medical diagnostic image (block 118) in an image storage system, such as the image storage systems 73, 102 and 104. The client 92 may then analyze the new medical diagnostic image (block 120) and also analyze various patient criteria and medical records (block 122) to determine if a temporal analysis of the new medical diagnostic image and one or more old images is desired (block 124).

This analysis (block 124) may be performed manually by a physician, automatically by the interface 96 on the client-side, or by the processing system 84. For example, the image processing scheme 114 may automatically evaluate patient medical records, the patient's age, and various other criteria to determine whether a temporal analysis of the old and new images is desirable for the treatment of the patient. If it is determined that temporal analysis is not desired, then the image processing scheme 114 ends (block 126) and no further temporal analysis of the images is performed. However, if it is determined that temporal analysis is desired, then the image processing scheme 114 proceeds to compress the new medical diagnostic image (block 128) using compression techniques, such as those illustrated in FIG. 5. Once the new medical diagnostic image has been compressed (block 128), then the image processing scheme 114 transmits the compressed new image to the remote processing system (block 130), such as the processing system 84 of the data processing center 22. The image also may be encrypted, or otherwise electronically secured, prior to transmission.

Temporal analysis of medical diagnostic images requires both the new medical diagnostic image and also one or more old medical diagnostic images, which may be associated with the same or different medical modalities. Accordingly, the image processing scheme 114 then proceeds to locate one or more old images for the subject being evaluated by the present technique. The image processing scheme 114 determines if there is an old medical diagnostic image stored locally on the image storage system of the client 92. If there is an old medical diagnostic image stored locally (block 132), then the image processing scheme 114 proceeds to determine whether there are multiple old images stored locally (block 134). If there is only one old medical diagnostic image stored locally, then the image processing scheme 114 proceeds to compress the old medical diagnostic image (block 136). Once the old image has been compressed into the desired format, the compressed old image is transmitted from the client 92 to the processing system via the network (block 138). Again, encryption or other security measures also may be used for the electronic transmission. If the image processing scheme 114 determines that there are multiple old medical diagnostic images (block 134), then the scheme 114 proceeds to analyze various selection criteria for choosing the best old image for the image processing (block 140). For example, as discussed above, the image processing scheme 114 may evaluate the dates of the images, the size and location of the images, the quality of the images, the medical diagnostic systems used to obtain the images, and various other factors. Once the image processing scheme 114 has analyzed the selection criteria (block 140), the scheme 114 proceeds to select a desired old image (block 142) for comparison and processing along with the new image at the processing system 84. The desired old image (block 142) selected by the scheme 114 is then compressed (block 136) and is transmitted to the processing system (block 138). The processing system 84 can then proceed to perform various temporal processing routines 170 on the old and new medical diagnostic images, which may include images from different modalities.

If the image processing scheme 114 determines that there is not a local old image (block 132), then the scheme 114 searches for old medical diagnostic images on remote image storage systems (block 144). For example, the processing system 84 may search for images of a specific patient at all medical facilities having the remote image storage systems and desired medical diagnostic imaging systems, which may have provided images of the desired physiological features of the patient. The image processing scheme 114 may or may not discover old desired images for the patient (block 146). If the scheme 114 does not discover old images for the patient (block 146), then the image processing scheme 114 terminates image processing of the new image for the patient (block 126).

If old images are discovered for the patient (block 146), then the image processing scheme 114 proceeds to determine if there are multiple old images disposed on the various remote image storage systems (block 148). If multiple old images exist (block 148), then the scheme 114 proceeds to determine whether the remote image storage systems have interfaces, such as a uniform interface or thin client interface, which are configured for platform independently interacting with the processing system (block 150). If the scheme 114 determines that the multiple old images are disposed on processing systems that include the desired interface (block 115), then the scheme 114 proceeds to analyze the selection criteria for the old images (block 140). The scheme 114 then selects the desired old image based on the selection criteria (block 142), compresses the selected old image (block 136), and transmits the selected and compressed old image to the processing system (block 138).

However, if the image processing scheme 114 determines that the multiple old images are disposed on remote image storage systems that lack the desired interface (block 150), then the scheme 114 proceeds to retrieve all of the multiple old images (block 152) and then to analyze the various selection criteria for the old images (block 154) at the processing system 84. Once the image processing scheme 114 has analyzed the selection criteria (block 154), then the scheme 114 proceeds to select the desired old image from the multiple old images (block 156), to compress the selected old image (block 158), and then to process the images at the processing system 84.

If the image processing scheme 114 determines that there is only a single remote old disposed on one of the remote image storage systems (block 148), then the scheme 114 proceeds to determine if an interface for the processing system is disposed on the remote image storage system having the discovered old image (block 160). If the remote image storage system has the desired interface for the processing system (block 160), then the image processing scheme 114 proceeds to compress the discovered old image (block 166). The scheme 114 then transmits the discovered and compressed old image to the processing system for image processing along with the compressed new image (block 168). However, if the scheme 114 determines that the remote image storage system does not have the desired interface (block 160), then the scheme 114 proceeds to retrieve the old image discovered by the processing system (block 162). The scheme 114 then compresses the old image (block 164) for image processing along with the compressed new image at the processing system 84.

After the processing system 84 has gathered the desired old and new medical diagnostic images (block 169), then the image processing scheme 114 proceeds with the desired temporal processing routines (block 170). The processing routines may include a variety of standard and custom image processing routines. In an exemplary embodiment of the image processing scheme 114, the temporal processing routines 170 include registering and matching the old and new images gathered at the processing system (block 172). The registering and matching steps also may involve deforming one or more of the old and new images. For example, it may be desirable to deform the older image to have the corresponding physiological features geometrically matched with the corresponding physiological features of the new image. Similarly, images from multiple modalities may be normalized (erg., to a common coordinate system and geometries for specific features) or otherwise matched to facilitate temporal subtraction of the desired physiological features. Also, it is desirable to have higher accuracy of the new image, which may have various changes (e.g., a tumorous growth) that the patient and physician would like to analyze and review. After the old and new images are registered/matched (block 172), the temporal processing routines 170 proceed to subtract the old and new images (block 174) to obtain a processed image to temporally changed features (block 176). Accordingly, the registering/matching and subtraction routines generate a subtracted image, which highlights tumors, cancerous growths, and other physiological changes occurring over time.

It should also be noted that the temporal processing routines 170 are performed in compressed formats of the old and new images. However, the image processing scheme 114 may compress or decompress the old and new images to any desired resolution or quality prior to performing the temporal processing routines 170. Accordingly, the old and new images may be processed in any desired resolution and compression format, while the image processing scheme 114 utilizes image compression to facilitate efficient network transfers over the network between the client 92 and the data processing center 22. After the scheme 114 completes the desired temporal processing routines 170, the processed image is transmitted to the client for further analysis (block 178). This transmission also may involve data compression and encryption, as discussed above. The additional analysis may include viewing the processed image (block 180), and also evaluating the processed image against the new image, the old image and various other patient medical information.

Figure 5:
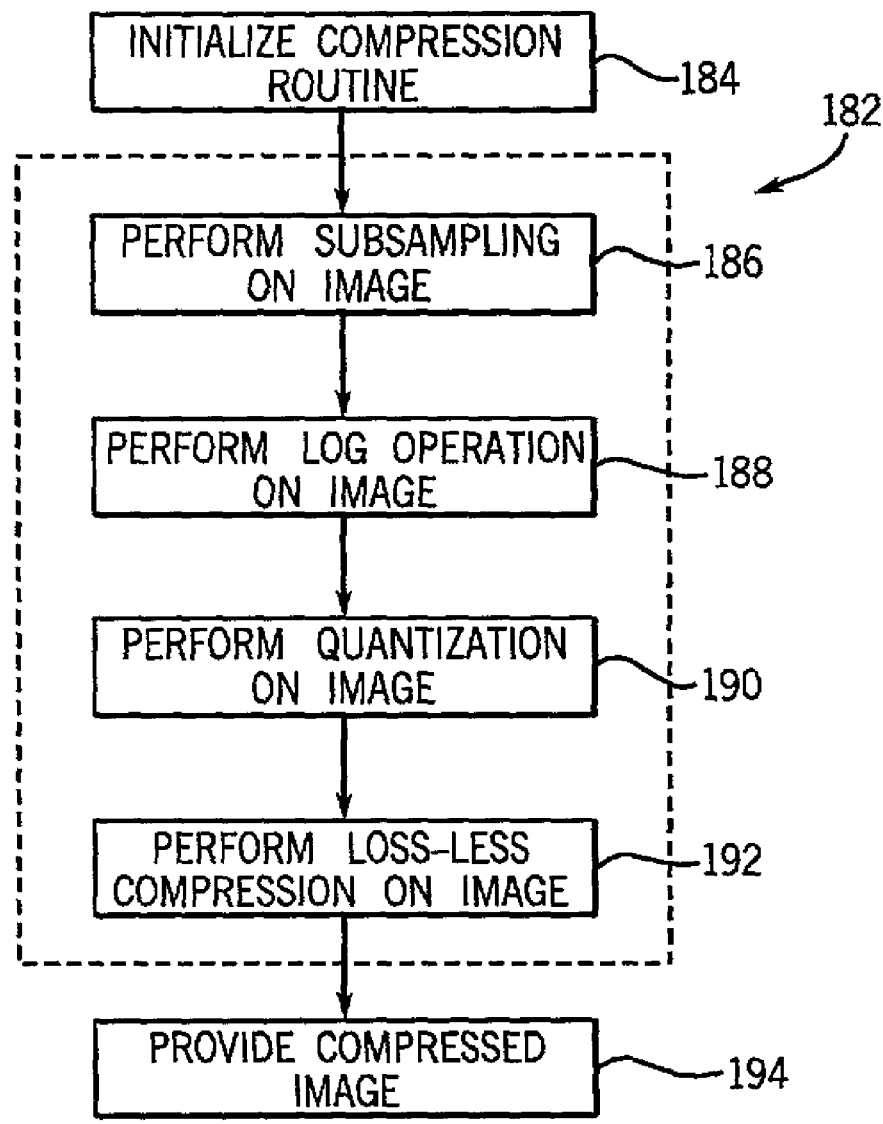
FIG. 5 is a flow chart illustrating an exemplary image compression routine of the present technique.

As discussed above, the present technique may utilize a variety of compression techniques to facilitate remote image processing of medical diagnostic images at the processing system 84. FIG. 5 is a diagram of an exemplary image compression routine 182 that may be used within the scope of the present technique. As illustrated, the image compression routine 182 begins by initializing a compression routine (block 184) that performs a plurality of image processing steps to generate a desired compressed image. Accordingly, the image compression routine 182 may perform sub-sampling on the image (block 186), a log operation on the image (block 188), quantization on the image (block 190), loss-less compression on the image (block 192), and various other compression routines. The desired compression routines generate a compressed image (block 194), which has a substantially reduced data size to facilitate more efficient network transfers. For example, the image compression routine 182 may compress the image file by a factor ranging from 15–1 to 5–1.

Medical diagnostic images typically have a relatively large file size, such as 10 MB or 15 MB, which makes network transfers extremely slow and impracticable. Accordingly, the image compression routine 182 may compress this image down to a file size ranging from 500 KB to 2 MB. In this exemplary image compression routine, the 10 MB medical diagnostic image may be compressed to a file size of approximately 1 MB. However, as the network efficiencies and the medical diagnostic imaging systems are improved, the desired compression of the images may change along with the state of the compression routines available.

Various other standard and customized compression routines also may be utilized along with the routines 182 to obtain the desired compression of the medical diagnostic image(s). The sub-sampling routine (block 186) also may include a filtering operation and may have sub-sampling parameters between 2 and 8. A sub-sampling with a factor of 8 on images with an initial pixel pitch of 200 μm will provide a pixel size of 1.6 mm, which is sufficient to detect desired physiological features with sizes of 1 cm or more. At the same time, it reduces the overall number of pixels (hence the computational time) by a factor of 64. It should also be noted that the log operation (block 188) may involve a dynamic range reduction of the image. The logarithmic function is relevant because the image subtraction needs to work on the density images, which are the logarithm of the intensity images. In the case of an input dynamic range of 14 bits, the output dynamic range could vary between 8 bits and 12 bits. The present technique may reduce the dynamic range of the medical diagnostic image to 8 bits, which would be a significant range reduction since computer materials handle bytes of 8 bits. Accordingly, the various image compression routines 182 provide a desired compression ratio or image size reduction to facilitate efficient network transfers and remote processing by the processing system 84.

Figure 6:
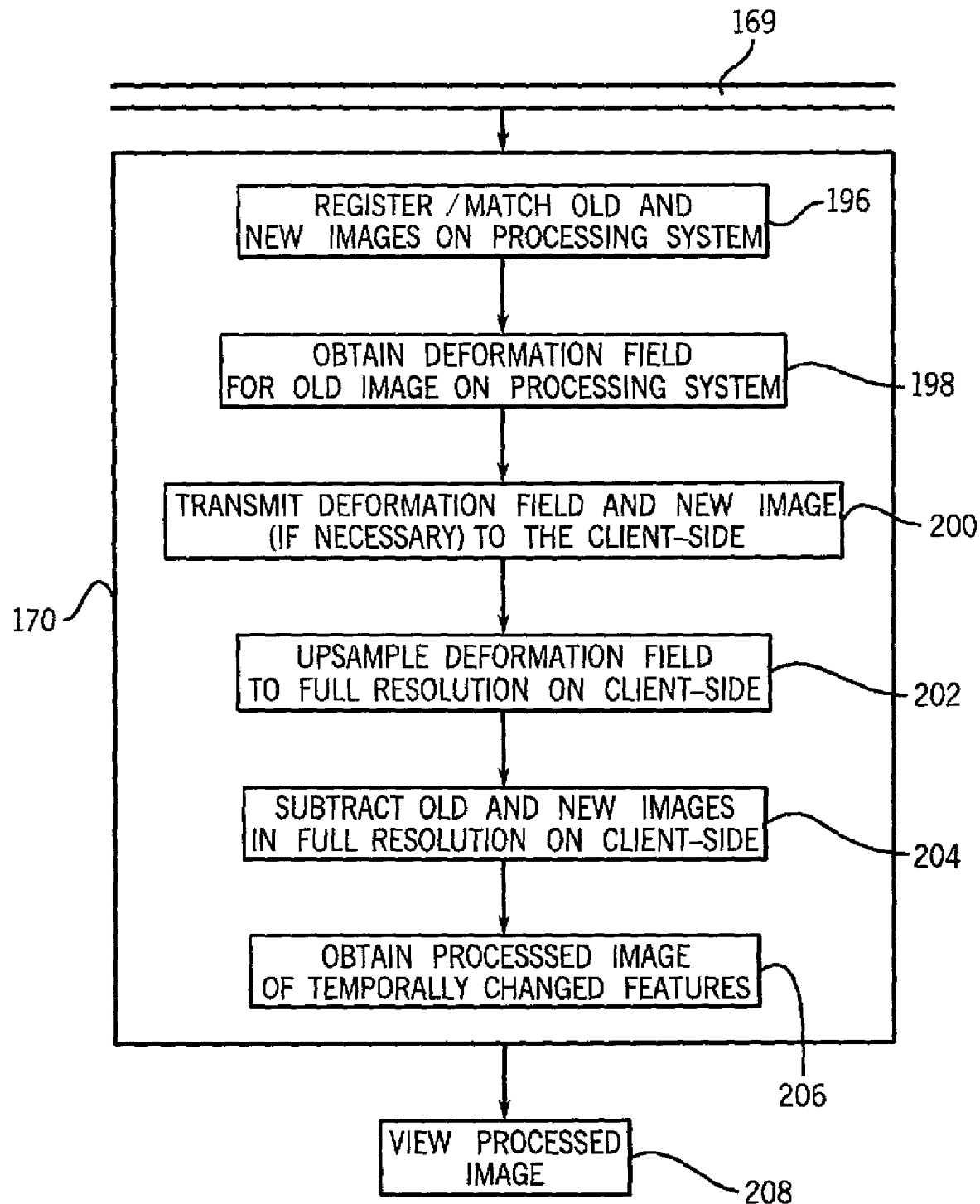
FIG. 6 is a flow chart illustrating an alternate processing routine of the present technique.

FIG. 6 is a diagram illustrating an alternate scheme for the temporal processing routines 170. As illustrated, the old and new medical diagnostic images may be registered/matched on the processing system (block 196) to obtain a deformation field for the old medical diagnostic image (block 198). The deformation field for the old medical diagnostic image and the new medical diagnostic image, if not already present on the client-side, may then be electronically transmitted to the client for completion of the temporal processing routine 170 on the client-side (block 200). At the client-side, the deformation field may then be up-sampled (or over-sampled) to full resolution (block 202). The old and new medical diagnostic images may then be subtracted in full resolution (block 204) on the client-side. Accordingly, a processed image of the temporarily changed features between the old and new medical diagnostic images is then obtained by the temporal processing routines (block 206). The client 92 may then view the processed image (block 208) via the interface 96.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives failing within the spirit and scope of the invention as defined by the following appended claims. For example, the invention may be utilized for image processing between multiple modalities and remote clients, while a variety of image compression, encryption, and processing applications may be utilized to provide a temporal analysis of the desired images.

The invention claimed is:

1. A method for processing images produced by medical diagnostic imaging systems, comprising:
    compressing at least one image of a plurality of temporally distinct medical images of desired physiological features;
    transmitting the plurality of temporally distinct medical images to a remote processing system via a network, wherein transmitting the plurality of medical images comprises communicating with the remote processing system via a uniform interface for the remote processing system; and
    generating an image from the plurality of temporally distinct medical images to highlight temporal differences of the desired physiological features between the image pair, wherein generating the image comprises geometrically matching the desired physiological features in at least two of the plurality of temporally distinct medical images.

2. The method of claim 1, wherein compressing the at least one image comprises compressing a new medical image obtained by a medical diagnostic imaging system.

3. The method of claim 1, wherein compressing the at least one image comprises reducing resolution of the at least one image.

4. The method of claim 1, wherein compressing the at least one image comprises subsampling the at least one image.

5. The method of claim 1, wherein compressing the at least one image comprises performing dynamic range reduction on the at least one image.

6. The method of claim 1, wherein compressing the at least one image comprises performing loss-less compression on the at least one image.

7. The method of claim 1, wherein compressing the at least one image comprises reducing memory consumption of the at least one image by a ratio of between 15:1 to 5:1.

8. The method of claim 7, wherein reducing memory consumption comprises reducing the at least one image to a file size between approximately 500 KB and approximately 2 MB.

9. The method of claim 1, wherein compressing the at least one image comprises increasing electronic transfer speeds for network transfers of the at least one image.

10. The method of claim 1, wherein transmitting the plurality of temporally distinct medical images comprises initiating an image processing request at the uniform interface for remotely processing the plurality of temporally distinct medical images at the remote processing system.

11. The method of claim 1, wherein transmitting the plurality of temporally distinct medical images comprises gathering medical images from a plurality of image storage systems at medical institutions.

12. The method of claim 11, wherein transmitting the plurality of temporally distinct medical images comprises initiating an image search at the remote processing system to retrieve medical images having the desired physiological features at the plurality of image storage systems.

13. The method of claim 1, wherein transmitting the plurality of temporally distinct medical images comprises encrypting data being transmitted via the network.

14. The method of claim 1, wherein geometrically matching the desired physiological features comprises deforming an older image of the plurality of temporally distinct medical images.

15. The method of claim 1, comprising performing image subtraction between at least two of the plurality of temporally distinct medical images.

16. The method of claim 1, wherein generating the image comprises processing the plurality of temporally distinct medical images in compressed formats.

17. The method of claim 1, wherein generating the image comprises processing at least two of the plurality of temporally distinct medical images at the remote processing system.

18. The method of claim 17, comprising transmitting the image to a client remote from the remote processing system via the network.

19. The method of claim 1, comprising automatically evaluating medical criteria and selecting a desired old image from a set of old images from the plurality of temporally distinct medical images.

20. The method of claim 1, comprising automatically evaluating medical criteria and determining whether to initiate a temporal analysis of a new image with an old image of the plurality of temporally distinct medical images.

21. The method of claim 1, comprising transmitting a report of the temporal differences to a client via the network.

22. The method of claim 1, comprising obtaining the plurality of temporally distinct medical images from multiple medical modalities.

23. The method of claim 1, wherein communicating with the remote processing system via the uniform interface comprises interacting between a thin client and an applications service provider.

24. The method of claim 23, wherein transmitting the plurality of temporally distinct medical images comprises gathering medical images from a plurality of image storage systems at medical institutions.

25. The method of claim 24, wherein transmitting the plurality of temporally distinct medical images comprises initiating an image search at the remote processing system to retrieve medical images having the desired physiological features at the plurality of image storage systems.

26. The method of claim 25, comprising automatically evaluating medical criteria and determining whether to initiate a temporal analysis of a new image with an old image of the plurality of temporally distinct medical images.

27. A method for temporal analysis of medical diagnostic images, comprising:
   compressing a plurality of temporally distinct medical diagnostic images of desired physiological features;
   electronically transmitting the plurality of temporally distinct medical diagnostic images to a remote processing system, wherein electronically transmitting the plurality of temporally distinct medical diagnostic images comprises communicating with the remote processing system via a uniform interface for the remote processing system;
   geometrically matching the desired physiological features of at least two images of the plurality of temporally distinct medical diagnostic images at the remote processing system; and
   generating an image from the at least two images to highlight physiological differences between the at least two images.

28. The method of claim 27, wherein compressing the plurality of temporally distinct medical diagnostic images comprises reducing image resolution.

29. The method of claim 27, wherein compressing the plurality of temporally distinct medical diagnostic images comprises reducing memory consumption by a ratio between approximately 15:1 and approximately 5:1.

30. The method of claim 29, wherein reducing memory consumption comprises reducing memory consumption to less than approximately 1.5 MB. comprises reducing memory consumption to less than approximately 1.5 MB.

31. The method of claim 27, wherein compressing the plurality of temporally distinct medical diagnostic images comprises reducing network transfer times to facilitate remote image processing.

32. The method of claim 27, wherein electronically transmitting the plurality of temporally distinct medical diagnostic images comprises electronically securing the plurality of temporally distinct medical diagnostic images to prevent unwanted access.

33. The method of claim 27, wherein electronically transmitting the plurality of temporally distinct medical diagnostic images comprises remotely searching a plurality of remote image storage systems for medical images having the desired physiological features.

34. The method of claim 27, wherein geometrically matching the desired physiological features comprises deforming a relatively older image of the at least two images.

35. The method of claim 34, wherein generating the image comprises subtracting the relatively older image from a newer image of the at least two images via an image subtraction routine disposed on the remote processing system.

36. The method of claim 35, comprising electronically transmitting the image to a remote client.

37. The method of claim 27, comprising automatically evaluating medical criteria and selecting a desired old image from a set of old images from the plurality of temporally distinct medical diagnostic images.

38. The method of claim 27, comprising automatically evaluating medical criteria and determining whether to initiate a temporal analysis of a new image with an old image of the plurality of temporally distinct medical diagnostic images.

39. The method of claim 27, comprising transmitting a report of the physiological differences to a client via a network.

40. The method of claim 27, wherein geometrically matching the desired physiological features of the at least two images comprises coordinating output from multiple imaging modalities.

41. A method for remotely performing a comparative analysis of a plurality of medical diagnostic images obtained over a time period, comprising:
   gathering medical diagnostic images at a remote processing system via a network, wherein gathering the medical diagnostic images comprises interacting with a remote image storage system via a uniform interface configured for interacting with the remote processing system and further comprises gathering images having desired physiological features from a plurality of remote image storage systems; and
   processing at least two images of the medical diagnostic images at the remote processing system to generate a temporal analysis image illustrating physiological differences between the at least two images.

42. The method of claim 41, wherein gathering medical diagnostic images comprises compressing at least one image of the medical diagnostic images prior to an electronic transfer over the network.

43. The method of claim 42, wherein compressing the at least one image comprises reducing image resolution of the at least one image.

44. The method of claim 42, wherein compressing the at least one image comprises reducing memory consumption of the at least one image by a ratio of greater than 5:1.

45. The method of claim 42, wherein compressing the at least one image comprises reducing memory consumption of the at least one image to a desired size based on network transmission efficiencies.

46. The method of claim 41, wherein gathering the medical diagnostic images comprises receiving an image processing request from the uniform interface configured for interacting with the remote processing system.

47. The method of claim 41, wherein processing the at least two images comprises geometrically matching desired physiological features in the at least two images.

48. The method of claim 41, wherein processing the at least two images comprises subtracting a first image of the at least two images from a second image of the at least two images.

49. The method of claim 41, wherein processing the at least two images comprises generating the temporal analysis at least partially at the remote processing system.

50. The method of claim 41, wherein processing the at least two images comprises processing the at least two images in compressed formats.

51. The method of claim 41, wherein processing the at least two images comprises coordinating output from imaging systems for multiple medical modalities.

52. The method of claim 41, comprising securely communicating image data between a client and the remote processing system via the network.

53. The method of claim 52, comprising encrypting the image data.

54. The method of claim 41, comprising transmitting results of the processing to a remote client via the network.

55. The method of claim 52, comprising automatically evaluating medical criteria and selecting a desired old image from a set of old images from the medical diagnostic images.

56. The method of claim 41, comprising automatically evaluating medical criteria and determining whether to initiate a temporal analysis of a new image with an old image of the medical diagnostic images.

57. A system for remotely processing medical diagnostic images, comprising:
 a remote processing system configured to compare a plurality of medical images and to highlight temporal differences between at least two images of the plurality of medical images, wherein the remote processing system comprises a modality matching module configured to coordinate imaging data obtained from different medical imaging modalities;
 a uniform interface for interacting with the remote processing system via a network; and
 an image compression module accessible by the uniform interface configured to compress at least one image of the plurality of medical images.

58. The system of claim 57, wherein the remote processing system comprises an image matching module configured for geometrically matching the desired physiological features in the at least two images.

59. The system of claim 58, wherein the image matching module comprises an image deformation module configured for altering one of the at least two images.

60. The system of claim 58, wherein the remote processing system comprises an image subtraction module configured for subtracting a first image from a second image of the at least two images.

61. The system of claim 57, wherein the remote processing system comprises an image search module configured for retrieving remote medical images from image storage systems coupled to the network.

62. The system of claim 57, wherein the remote processing system comprises an image compression module configured for compressing uncompressed images prior to image processing at the remote processing system.

63. The system of claim 57, wherein the uniform interface comprises a platform independent interface assembly.

64. The system of claim 63, wherein the platform independent interface assembly comprises a thin client.

65. The system of claim 57, wherein the uniform interface is coupled to an image storage system for at least one medical diagnostic imaging system in a medical institution.

66. The system of claim 57, comprising a plurality of uniform interfaces disposed at a plurality of medical institutions.

67. The system of claim 57, wherein the uniform interface has a processing request module configured for transmitting to the remote processing system a new image of the plurality of medical images and a request for temporal comparison with at least one old image of the plurality of medical images.

68. The system of claim 57, wherein the image compression module comprises compression routines configured for reducing memory consumption of the at least one image to a desired size based on network transfer efficiencies of the network.

69. The system of claim 68, wherein the desired size is less than approximately 1.5 MB.

70. The system of claim 68, wherein the compression routines comprise a subsampling routine.

71. The system of claim 68, wherein the compression routines comprise a dynamic range reduction routine.

72. The system of claim 68, wherein the compression routines comprise a loss-less compression routine.

73. The system of claim 57, comprising an image selection module configured for automatically evaluating medical criteria and selecting a desired old image from a set of old images from the plurality of medical images.

74. The system of claim 57, comprising an image processing decision module configured for automatically evaluating medical criteria and determining whether to initiate a temporal analysis of a new image with an old image of the plurality of medical images.

75. The system of claim 57, comprising a transmission security module configured for securely transmitting image data via the network.

76. A system for platform independent processing of medical diagnostic images, comprising:
 an applications server configured to execute temporal image analysis requests from remote platform independent interfaces, wherein the applications server comprises:
 an image matching module configured for geometrically matching desired physiological features in at least two images obtained over a time period; and
 an image subtraction module configured for subtracting a first image from a second image of the at least two images.

77. The system of claim 76, wherein the applications server comprises an image compression module configured for compressing uncompressed images of the at least two images prior to executing the temporal image analysis.

78. The system of claim 76, wherein the remote processing system comprises an image search module configured for retrieving remote medical images from image storage systems coupled to the network.

79. The system of claim 76, wherein the remote processing system comprises an image selection module configured for automatically evaluating medical criteria and selecting a desired old image from a set of old images from the at least two images.

80. The system of claim 76, wherein the remote processing system comprises an image processing decision module configured for automatically evaluating medical criteria and determining whether to execute the temporal image analysis of a new image with an old image of the at least two images.

81. The system of claim 76, wherein the image matching module comprises an image deformation module configured for altering one of the at least two images.

82. The system of claim 76, wherein the image matching module is configured for coordinating imaging data from different imaging modalities.

83. The system of claim 76, comprising a data encryption module.

84. A method for remotely performing a comparative analysis of a plurality of medical diagnostic images obtained over a time period, comprising:
 gathering medical diagnostic images at a remote processing system via a network, wherein gathering the medical diagnostic images comprises interacting with a remote image storage system via a uniform interface configured for interacting with the remote processing system; and
 processing at least two images of the medical diagnostic images at the remote processing system to generate a temporal analysis image illustrating physiological differences between the at least two images, wherein processing the at least two images comprises geometrically matching desired physiological features in the at least two images.

85. A system for remotely processing medical diagnostic images, comprising:

a remote processing system configured to compare a plurality of medical images and to highlight temporal differences between at least two images of the plurality of medical images;

a uniform interface for interacting with the remote processing system via a network; and an image compression module accessible by the uniform interface configured to compress at least one image of the plurality of medical images, wherein the image compression module comprises compression routines configured for reducing memory consumption of the at least one image to a desired size based on network transfer efficiencies of the network.

* * * * *